United States Patent [19]

Kim et al.

[11] Patent Number: 5,589,394
[45] Date of Patent: Dec. 31, 1996

[54] CELL SUSPENSION PREPARATION APPARATUS AND METHOD

[75] Inventors: Young R. Kim, Sunnyvale; Kenneth E. Iles, Los Altos; Roderick W. Larue, Sebastopol, all of Calif.

[73] Assignee: Abbott Laboratories, Abbott Park, Ill.

[21] Appl. No.: 356,412

[22] Filed: Dec. 15, 1994

Related U.S. Application Data

[63] Continuation-in-part of Ser. No. 283,379, Aug. 1, 1994, abandoned.

[51] Int. Cl.$^6$ .................................................. H01N 35/10
[52] U.S. Cl. .................. 436/63; 436/43; 436/54; 436/174; 436/179; 436/180; 422/63; 422/68.1; 422/73; 366/145; 366/146; 366/219
[58] Field of Search ............................. 422/63, 68.1, 73, 422/81, 100, 102, 104; 435/290, 315, 316, 809; 436/43, 49, 54, 174, 179, 180, 63; 366/208, 209, 145, 146, 210, 211, 213, 219, 237

[56] References Cited

U.S. PATENT DOCUMENTS

| | | | |
|---|---|---|---|
| 3,790,346 | 2/1974 | Ritchie | 422/64 |
| 3,790,760 | 2/1974 | Stiller | 422/73 |
| 3,876,379 | 4/1975 | Ghim | 422/73 |
| 4,130,395 | 12/1978 | Chryssanthou | 422/64 |
| 4,200,607 | 4/1980 | Suzuki | 422/64 |
| 4,518,264 | 5/1985 | Nohso | 366/208 |
| 4,539,296 | 9/1985 | Manabe | 436/47 |
| 4,858,155 | 8/1989 | Okawa et al. | 364/557 |
| 4,876,069 | 10/1989 | Jochimsen | 422/73 |
| 4,964,728 | 10/1990 | Kloth et al. | 356/427 |
| 4,983,359 | 1/1991 | Tomioka et al. | 422/81 |
| 5,104,231 | 4/1992 | Collier et al. | 366/208 |
| 5,215,714 | 6/1993 | Okada et al. | 422/64 |
| 5,223,398 | 6/1993 | Kortright et al. | 435/7.24 |
| 5,238,812 | 8/1993 | Coulter et al. | 435/7.2 |
| 5,266,269 | 11/1993 | Niiyama et al. | 422/73 |

*Primary Examiner*—Long V. Le
*Attorney, Agent, or Firm*—Mark C. Bach

[57] ABSTRACT

Embodiments described herein provide apparatuses and methods for preparing fluid. In one method, a heater thermally associated with a housing for receiving fluid is operated to apply thermal energy to the housing. A second predetermined volume of a second fluid is introduced to the housing. The second predetermined volume of the second fluid is moved with the housing for a first predetermined time period. The first predetermined volume of the first fluid is introduced to the housing. The first predetermined volume of first fluid and the second predetermined volume of second fluid are moved with the housing for a second predetermined time period. The first predetermined volume of first fluid and the second predetermined volume of second fluid are removed from the housing. Another embodiment provides an apparatus comprising a first housing for containing fluid. A second housing is operatively connected with the first housing. A prime mover is fixedly-attached to the second housing and is operatively connected with the first housing such that the first housing moves responsive to the prime mover and such that the second housing remains substantially stationary with respect to the prime mover. A fluid inlet is fluidly connected with the first housing for supplying fluid to the first housing. A fluid outlet is fluidly connected with the first housing for removing fluid from the first housing.

24 Claims, 6 Drawing Sheets

CELL SUSPENSION PREPARATION APPARATUS AND METHOD

REFERENCE TO RELATED APPLICATIONS

This is a continuation-in-part application of Ser. No. 08/283,379 filed Aug. 1, 1994 entitled METHOD AND APPARATUS FOR PERFORMING AUTOMATED ANALYSIS, now abandoned. The parent application is assigned to the assignee of this case. The disclosure of the parent application is incorporated herein in its entirety by this reference.

BACKGROUND OF THE INVENTION

Embodiments described herein relate generally to an apparatus for preparing a fluid and a method of preparing a fluid. More specifically, the embodiments relate to a sample preparation apparatus and method which relatively quickly prepares a whole blood sample for medical tests, such as a white blood cell differential, immuno-phenotyping and the like, performed by an automated analytical instrument.

Automated analytical instruments are available to perform a number of tasks. For instance, the automated instrument may perform a number of tests on a fluid, a biological sample and the like. In some embodiments, the fluid on which the tests are performed is a whole blood sample. The tests performed on the whole blood sample can be used to determine health status of an individual from whom the whole blood sample came.

To perform the tests on the whole blood sample, a portion of the whole blood sample may be mixed with another fluid, such as a reagent and the like. The whole blood sample, or the whole blood sample mixed with the another fluid, is sent to a detector. The detector measures or detects presence of an item of interest in the whole blood sample. The item of interest may be a cell, a particle and the like. The detector "reads" the sample and reports data to a computer. The computer processes the data and reports a result, which indicates presence of the item of interest in the whole blood sample, to an operator of the instrument.

To prepare the whole blood sample to be sent to the detector, a fluid preparation apparatus and method of sorts may be used. A portion of the whole blood may be mixed with another fluid to remove parts of the blood, such as red cells. To remove the red cells, while preserving white cell morphology, the another fluid and the whole blood may have to stay together or be incubated for a time period of about 3 to 10 minutes at a temperature of about 40 degrees Celsius or greater. The demand on blood tests may be relatively high. It may not be desirable to wait about 5 to 10 minutes to begin a blood test. Also, it may be difficult to keep the blood sample and the another fluid at the desired temperature for the desired time.

SUMMARY OF THE INVENTION

Embodiments described herein provide apparatuses and methods for preparing fluid. In one method, a heater thermally associated with a housing for receiving fluid is operated to apply thermal energy to the housing. A second predetermined volume of a second fluid is introduced to the housing. The second predetermined volume of the second fluid is moved with the housing for a first predetermined time period. The first predetermined volume of the first fluid is introduced to the housing. The first predetermined volume of first fluid and the second predetermined volume of second fluid are moved with the housing for a second predetermined time period. The first predetermined volume of first fluid and the second predetermined volume of second fluid are removed from the housing.

Another embodiment provides an apparatus comprising a first housing for containing fluid. A second housing is operatively connected with the first housing. A prime mover is fixedly attached to the second housing and is operatively connected with the first housing such that the first housing moves responsive to the prime mover and such that the second housing remains substantially stationary with respect to the prime mover. A fluid inlet is fluidly connected with the first housing for supplying fluid to the first housing. A fluid outlet is fluidly connected with the first housing for removing fluid from the first housing.

A further embodiment provides an apparatus with a housing for containing fluid. A heater is thermally connected with the housing for applying thermal energy to the housing and the fluid contained in the housing. A prime mover is operatively connected with the housing to move the housing and the fluid contained in the housing.

Still another embodiment provides a method in which fluid is placed within a housing. Thermal energy is applied to the housing and the fluid within the housing. The housing and the fluid contained in the housing are moved.

DETAILED DESCRIPTION OF PREFERRED EMBODIMENTS

Figure 1:
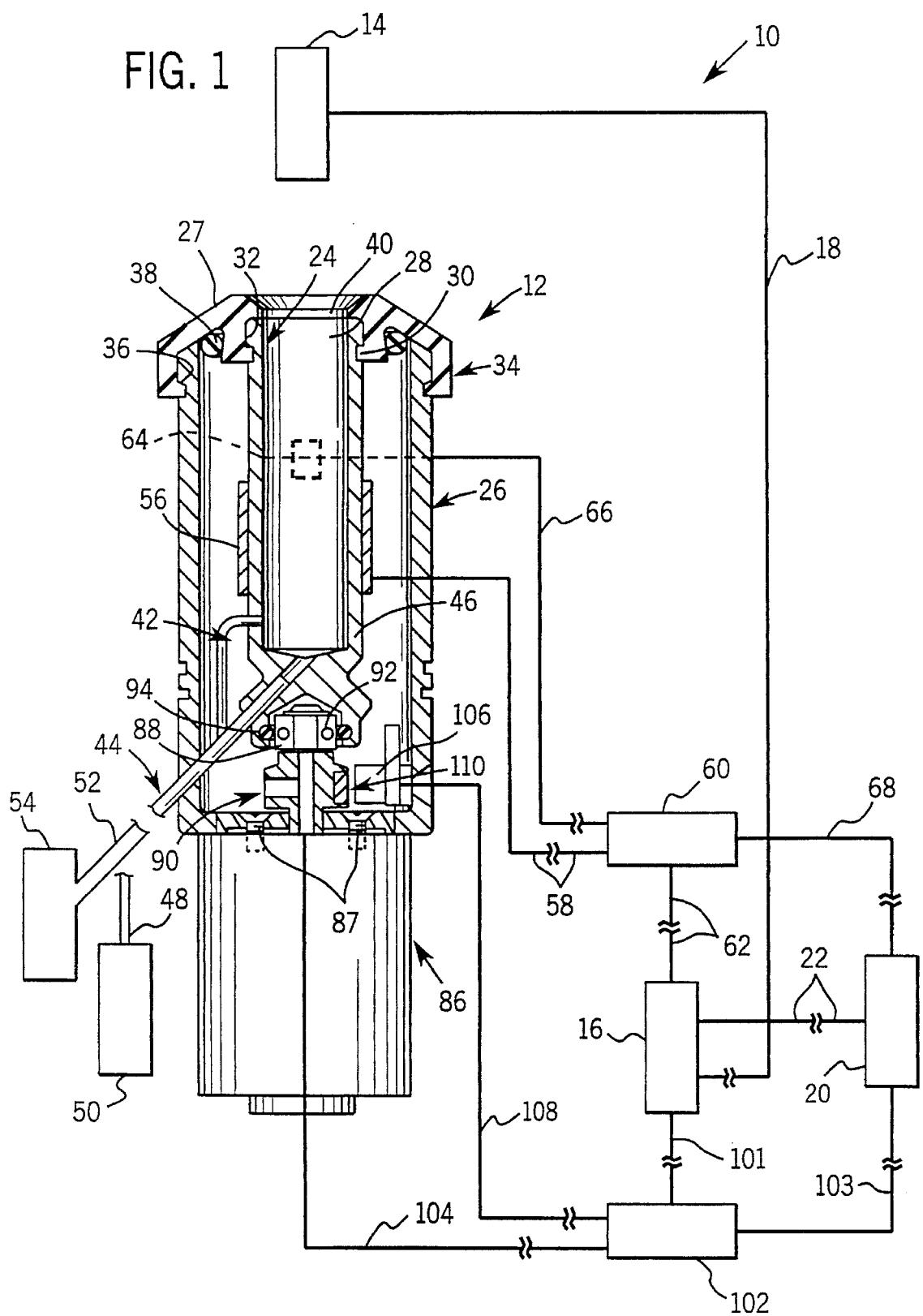
FIG. 1 is a schematic diagram of a sample preparation apparatus described herein.

One embodiment illustrated in FIG. 1 provides an apparatus 10 and a method for preparing a fluid or sample, such as a whole blood sample and the like. For the sake of clarity of understanding, the apparatus 10 and the method will be discussed with respect to employment in an automated analytical instrument, such as the instrument disclosed in the above-referenced U.S. patent application, and the like. To further facilitate understanding, in the exemplary embodiments discussed below, the fluid being prepared is whole blood. However, other fluids may be used. Also, elements of one embodiment may be combined with elements of another embodiment to arrive at yet further embodiments. For instance, method steps from one method may be combined with method steps from another method to produce yet a further method.

The apparatus 10 generally includes a fluid preparer 12, a fluid introducer 14 and a controller 16. The fluid preparer 12 is operatively associated with the fluid introducer 14 such that the fluid introducer 14 introduces a first fluid, such as a whole blood sample, a cell suspension and the like, to the fluid preparer 12. The fluid introducer 14 is electrically connected with the controller 16 by conductor 18 so that the controller 16 monitors and coordinates operation of the fluid introducer 14. The controller 16 is electrically connected with a source 20 of electrical energy by conduit 22 for supplying the controller 16 with electrical energy. In an exemplary embodiment, the fluid introducer 14 is a pipettor operatively associated with a suitable source of fluid to be prepared by the apparatus 10. The controller 16 may be a computer having memory containing and running appropriate routines to control operation of the apparatus 10.

The illustrated embodiment of the fluid preparer 12 comprises a first or inner housing 24, a second or outer housing 26 and a joining member 27. The inner housing 24 and the outer housing 26 are substantially cylindrical and include open ends to facilitate introduction of fluid from the fluid introducer 14 into an interior 28 of the inner housing 24. The inner housing 24 and the outer housing 26 are disposed substantially coaxially with the inner housing 24 being disposed substantially within the outer housing 26.

Figure 3:
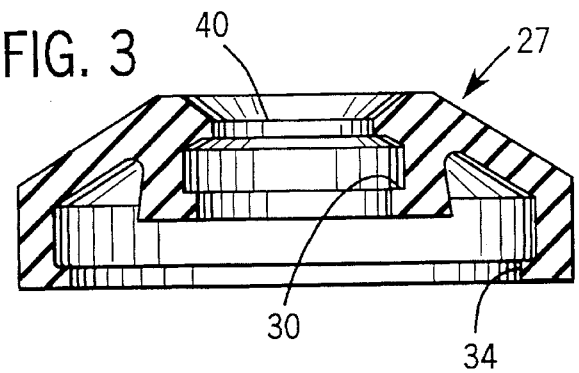
FIG. 3 is a partially sectioned view of another portion of the apparatus of FIG. 1.

The joining member 27, illustrated in FIGS. 1 and 3, substantially surrounds and operatively connects the open ends of the inner member 24 and the outer-member 26. The joining member 27 includes a first substantially annular projection 30 which mates with a substantially annular notch 32 on the inner member 24 adjacent its open end and a second substantially annular projection 34 which mates with a substantially annular notch 36 on the outer member 26 adjacent its open end. To facilitate retention of the projection 30 within the notch 32, an O-ring 38 is provided that substantially surrounds an outer diameter surface of the substantially annular projection 30. The O-ring 38 performs essentially as a spring clamp for substantially securing the projection 30 within the notch 32. The O-ring 38 maintains the open end of the inner housing 24 substantially stationary with respect to the open end of the outer housing 26 during operation of the apparatus 10.

In an exemplary embodiment, the outer housing 26 is made from a suitable polymer, such as DERLIN (white) and the like. In other embodiments, the outer housing 26 may be made of stainless steel. The outer housing 26 has an outer diameter of about 1.25 inches, an inner diameter of about 1.06 inches and an axial length of about 2.22 inches. An axial length of an interior of the outer member 26 is about 2.13 inches. A distal edge of the notch 36 is offset axially from the open end of the outer housing 26 by about 0.18 inches. The notch 36 is about 0.06 inches wide and defines an outer diameter of about 1.19 inches.

The inner housing 24 is made from a material that is non-reactive with the fluid being prepared by the apparatus 10. In an exemplary embodiment, the inner housing 24 is made from a suitable metal, such as 303 or 304 stainless steel and the like. The inner housing 24 has an outer diameter of about 0.65 inches, an inner diameter of about 0.5 inches and an axial length of about 1.94 inches. The interior 28 of the inner housing 24 has an axial length of about 1.5 inches. A distal edge of the notch 32 is offset axially from the open end of the inner housing 24 by about 0.127 inches. The notch 32 is about 0.06 inches wide and defines a diameter of about 0.56 inches.

In an exemplary embodiment, the joining member 27 is made from an elastomeric material, such as a silicon rubber and the like. In a particular embodiment, the silicon rubber may be RTV 615, RTV 632 or RTV 630 (available from General Electric), cured at about 302 degrees Fahrenheit for about 75 minutes and at about 212 degrees Fahrenheit for about 4 hours. The silicon rubber has a durometer reading substantially within the range of about 45 to about 70 with sufficient tear resistance. The particular formulation of silicon rubber used may be dependent upon the type of mold used to form the silicon rubber into the joining member 27.

The exemplary embodiment of the joining member 27 has an outer diameter of about 1.43 inches. An inner surface of the projection 34 defines a diameter measuring about 1.18 inches. An outer surface of the projection 30 defines a diameter of about 0.86 inches and an inner surface of the projection 30 defines a diameter measuring about 0.55 inches. The joining member 27 includes a fluid inlet or opening 40 which allows fluid to be introduced into the interior 28 of the inner housing 24. The opening 40 defines a diameter measuring about 0.49 inches.

The inner housing 24 includes structures for introducing fluid into and removing fluid from the interior 28 of the inner housing 24. Specifically, the inner housing 24 includes a fluid inlet 42 and a fluid outlet 44. In one embodiment, the fluid inlet 42 and the fluid outlet 44 may be made from stainless steel tubing. In another embodiment, the fluid inlet 42 may comprise a conduit, such as a coil and the like, disposed adjacent the inner housing 24 such that thermal energy can be transferred from the inner housing 24 to the conduit thereby applying thermal energy to the fluid prior to introduction to the interior 28 of the inner housing 24. The fluid inlet 42, in an exemplary embodiment, is offset axially about 1.43 inches from a distal end of the inner housing 24. The fluid outlet 44 is disposed substantially centrally on a proximal end 46 of the inner housing 24. To facilitate movement of fluid from the interior 28 of the inner housing 24 into the fluid outlet 44, the proximal end 46 is inclined or sloped from an axial wall of the inner housing toward the fluid outlet 44.

The fluid inlet 42 is fluidly connected by a suitable conduit 48 to a source 50 of second fluid, such as a lysing solution and the like, to be introduced into the interior 28 of the inner housing 24. The source 50 may include a mechanism, such as a syringe pump and the like, to positively move fluid from the source 50 through the conduit 48 to the fluid inlet 42 and the interior 28 of the inner housing 24. The fluid outlet 44 is fluidly connected by a suitable conduit 52 to a tank 54. The tank 54 may be another portion of an analytical instrument with which the apparatus 10 is operatively associated. In other embodiments, the tank 54 may retain fluid from the interior 28 of the inner housing 24 until needed for further processing.

In some embodiments, it may be desirable to maintain fluid within the interior 28 of the inner housing 24 at a desired temperature. This fluid may be from the fluid introducer 14, from the source 50 or a combination of fluids from the fluid introducer 14 and the source 50. To do this, a heating element 56 is operatively associated with the inner housing 24. In the illustrated embodiment, the heating element 56 is an electrical heating element, such as an etched foil heating element laminated between layers of a flexible insulating (electrical) material, having an electrical resistance substantially within the range of about 41Ω to about 72Ω. The heating element 56, in the illustrated embodiment, substantially surrounds and contacts a portion of an outer diameter surface of the inner housing 24. In this way, thermal energy generated by the heating element 56 is transferred to the inner housing 24 and from their to the contents, i.e. fluid, disposed in the interior 28 of the inner housing 24.

The heating element 56 is electrically connected by conductor 58 to a heater controller 60. The heater controller 60 applies appropriate electrical energy to the heating element 56 such that the desired amount of thermal energy is generated by the heating element 56 and applied to the inner housing 24.

To monitor thermal energy associated with the heating element 56 and the inner housing 24, a sensor 64 is provided operatively thermally connected with the heating element 56 and the inner housing 24. In an exemplary embodiment, a recess is formed on the inner housing 24 to accept the sensor 64 such that an outer profile of the inner housing 24 is substantially constant and smooth. In one embodiment, the sensor 64 is a resistance temperature detector, such as a thin film platinum resistance temperature detector like Model number S260PD available from Minco Products of Minneapolis, Minn. having a nominal resistance of about 100Ω at about 0 degrees Celsius and a temperature coefficient of resistivity of about 0.385Ω/° C. In an exemplary embodiment, the sensor 64 has a width of about 3 mm, a length of about 12 mm and a thickness of about 0.27 mm. The sensor 64 is electrically connected by conductor 66 to the heater controller 60. The heater controller 60, in turn, is electrically connected by conductor 62 to the controller 16 and to the source 20 of electrical energy by conductor 68.

Figure 5:
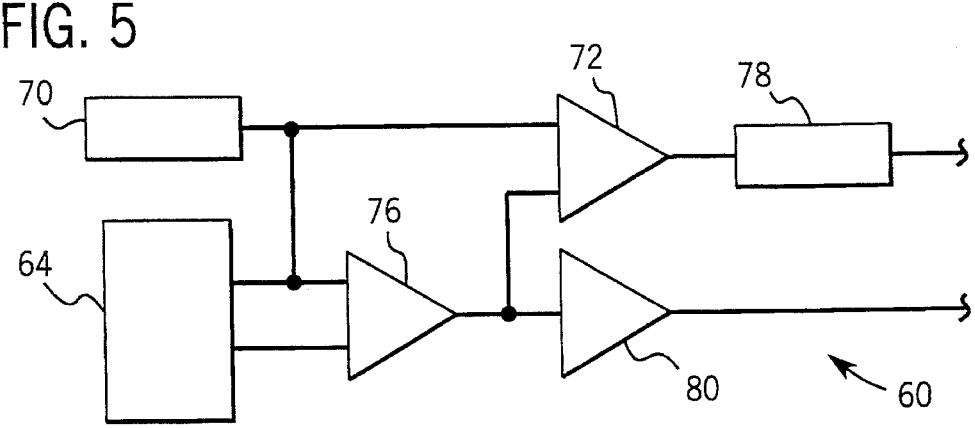
FIG. 5 is a block schematic diagram of another portion of the apparatus of FIG. 1.
Figure 7A:
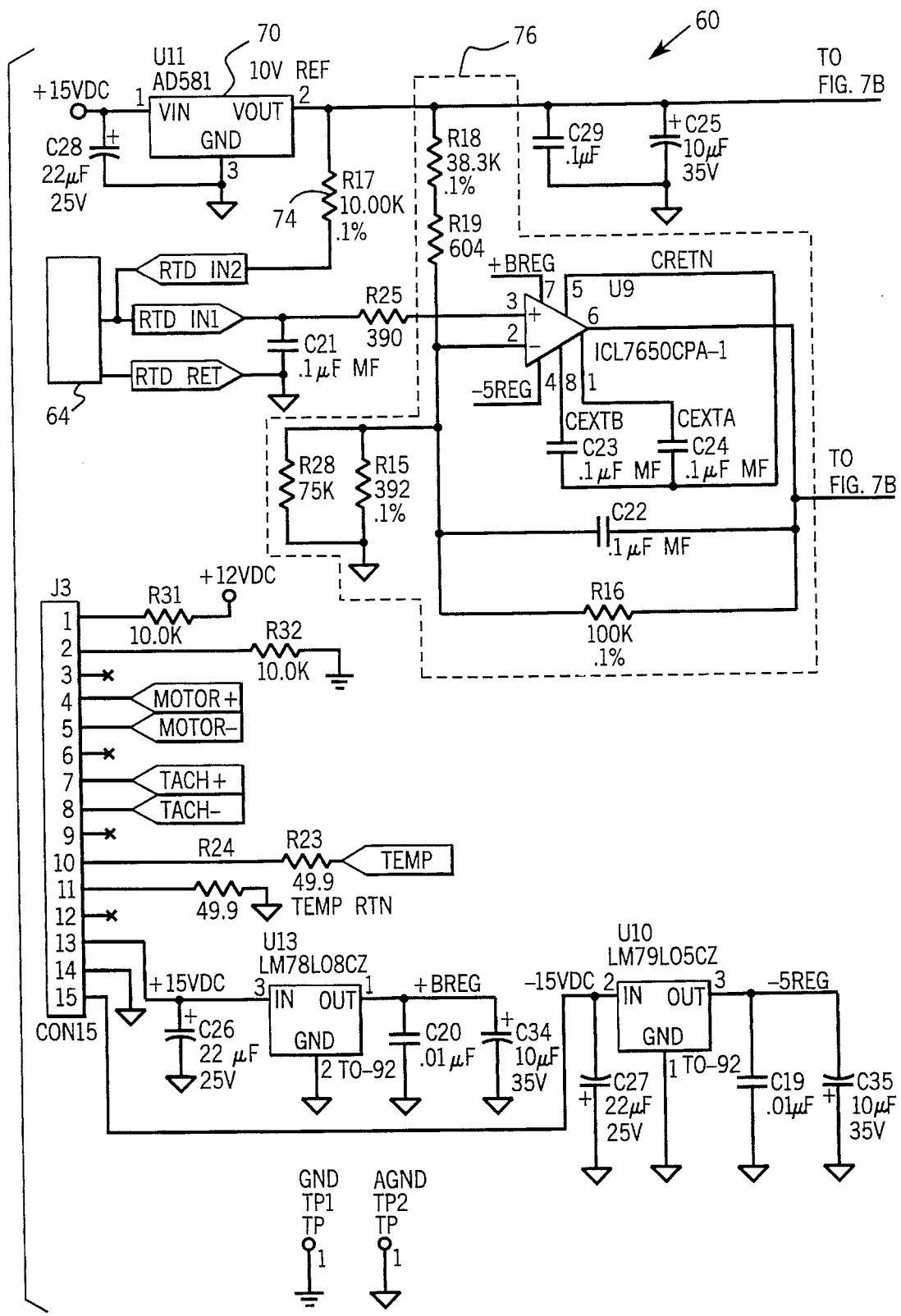
FIG. 7A and 7B are detailed schematic diagrams of the portion of the apparatus illustrated in FIG. 5.
Figure 7B:
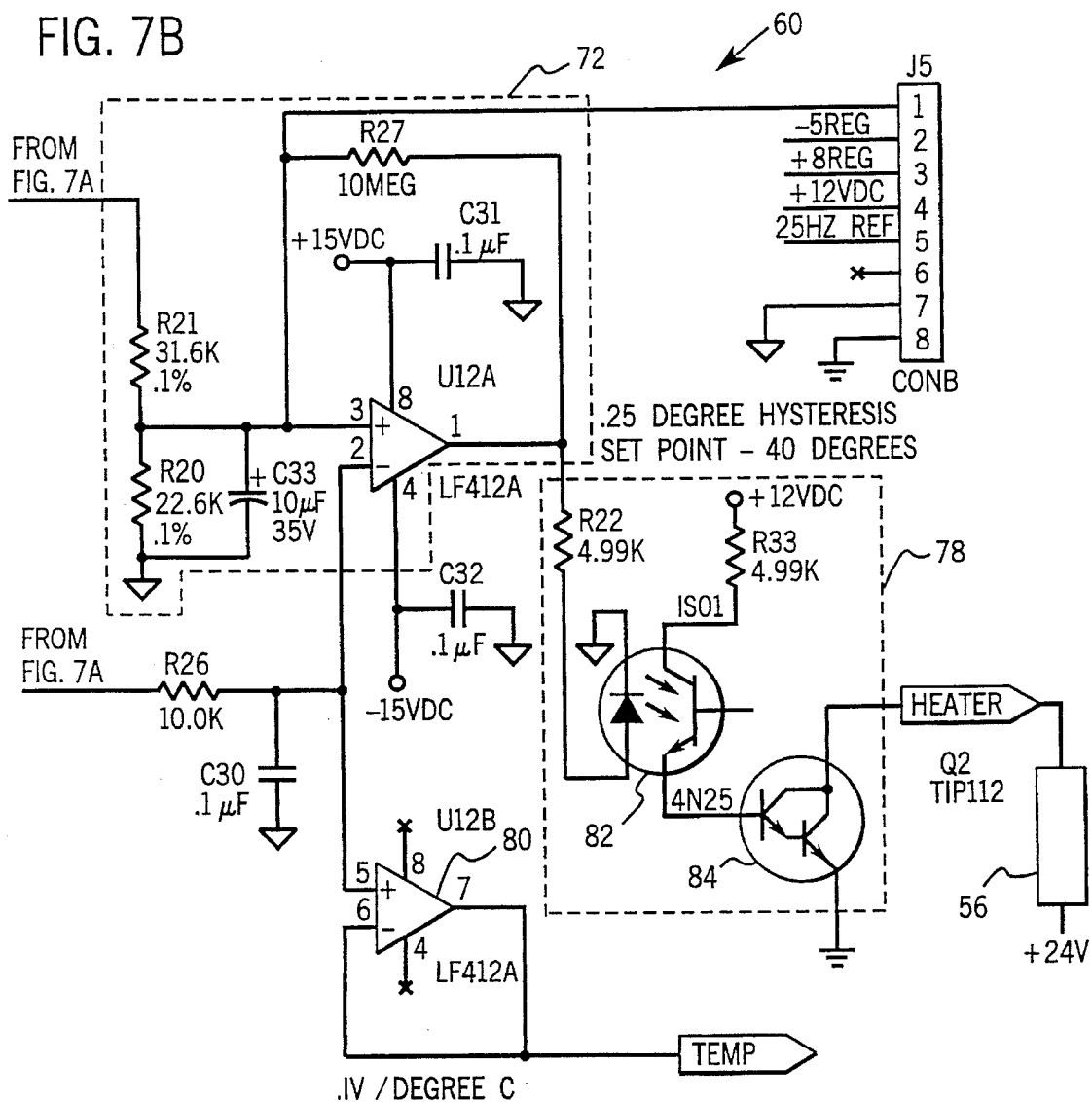

Construction of an exemplary embodiment of the heater controller 60 is illustrated more clearly in FIGS. 5 and 7. The heater controller 60 generally operates by comparing an electrical signal indicative of thermal energy associated with the inner housing 24 with a reference signal and using a result of the comparison to drive the heating element 56. A reference signal (about 10 Volts DC in this embodiment) is generated by a voltage source 70, which may be an AD581 voltage source. The approximately 10 Volt output from the voltage source 70 is applied to a comparator 72 and to the sensor 64. The sensor 64 forms a voltage divider with a series resistor 74 (FIG. 7) so that the voltage at an input to an amplifier 76 is a function of thermal energy associated with the sensor 64. Thus, the voltage applied to the amplifier 76 corresponds to a function of the thermal energy associated with the inner housing 24. The amplifier 76 applies an offset and a gain to the voltage from the sensor 64 so that the output from the amplifier 76 is an approximately linear function of the thermal energy associated with the inner housing 24. In an exemplary embodiment, the output of the amplifier 76 is (in Volts) about 0.1 times the thermal energy associated with the inner housing 24 (in degrees Celsius).

The output of the amplifier 76 is electrically connected to the comparator 72. The output voltage of the comparator 72 is sensed by a driver 78 which powers the heating element 56. In this embodiment, the output of the amplifier 76 is a negative input to a differential amplifier 80. The positive input of the differential amplifier 80 is a voltage of about 4.0 volts from a voltage divider powered from the about 10 Volt reference signal. In this embodiment, the output of the differential amplifier 80 is about zero when the thermal energy associated with the inner housing 24 is about 40 degrees Celsius. When the thermal energy associated with the inner housing 24 is less than about 40 degrees Celsius, the output of the amplifier 80 drops to less than about 4.0 Volts and the output voltage of the comparator 72 increases to a positive value. The increase in the output voltage of the comparator 72 causes current to flow through an optocoupler 82 (FIG. 7) which turns on a Darlington pair 84 to increase the current through the heating element 56. When the thermal energy associated with the inner housing 24 rises to about 40 degrees Celsius or more, the output of the comparator 72 becomes negative, turning off the current through the optocoupler 82 and, in turn, turning off the Darlington pair 84 and the heating element 56.

The inner housing 24 not only can maintain a fluid in the interior 28 at a desired thermal energy level, but also can combine or mix fluids, such as a first fluid from the fluid introducer 14 and a second fluid from the source 50, if desired. To facilitate fluid combination, a proximal end of the inner housing 24 is operatively connected with a prime mover 86 such that the inner housing 24 moves responsive to action of the prime mover 86. A proximal end of the outer housing 26 is fixed to the prime mover 86 by fasteners 87. In an exemplary embodiment, the prime mover 86 is a direct current electric motor, such as model no. LC22-107 available from SKC Shinano Kenshi Corp. of Culver City, Calif. This embodiment of the prime mover 86 operates at about 3,000 rpm's.

Figure 2:
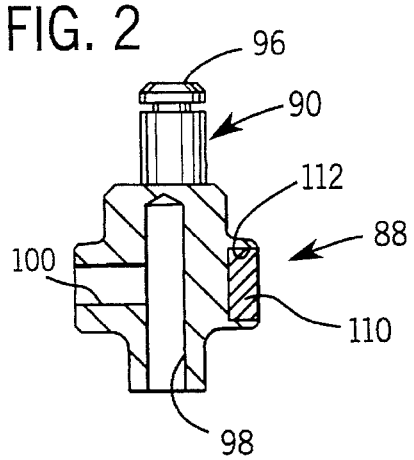
FIG. 2 is a partially sectioned view of a portion of the apparatus of FIG. 1.

A linkage assembly 88 operatively or drivingly connects the prime mover 86 with the inner housing 24. The linkage assembly 88 comprises a drive member 90 (FIG. 2) and a bearing 92. A shaft 96 on the drive member 90 is coupled with the bearing 92 by appropriate means, such as a lock washer retained about a groove in the shaft 96. The bearing 92 is coupled with the proximal end of the inner housing 24 by an O-ring 94 which provides a relatively soft, elastomeric cushioned mechanical coupling of bearing 92 to the inner housing 24. The O-ring 94 also elastomerically compensates for angular centerline displacement caused by movement (e.g. eccentric) only at the proximal end of the inner housing 24. As shown in FIG. 2, the shaft 96 is offset, by about 0.03 inches in an exemplary embodiment, from a midline of the drive member 90.

The drive member 90 includes a bore 98 for accepting a drive shaft, which is rotatable, associated with the prime mover 86 such that movement of the drive shaft of the prime mover 86 causes complementary movement of the drive member 90. Another bore 100, disposed substantially orthogonally to the bore 98, is provided in the drive member 90 for accepting a fastener which can bear against the drive shaft of the prime mover 86 such that the drive member 90 moves conjointly with the prime mover 86 drive shaft.

The inner housing 24 moves responsive to operation of the prime mover 86. The movement of the inner housing 24 is not identical to the rotary motion of the drive shaft of the prime mover 86. The motion of the inner housing 24 is defined, in part, by the offset disposition of the shaft 96 and the juncture between the open end of the inner housing 24 and the open end of the outer housing 26 provided by the joining member 27. Accordingly, the open ends of the inner housing 24 and the outer housing 26 remain substantially stationary with relative movement corresponding to flexibility provided by the elastomeric nature of the joining member 27. However, the proximal end of the inner housing 24 is free to move conjointly with the shaft 96 on the drive member, which moves responsive to movement of the drive shaft of the prime mover 86. Because the shaft 96 is disposed offset on the drive member 90, movement of the shaft 96 generally follows a substantially eccentric path. Thus, the inner housing 24 generally "vibrates" responsive to operation of the prime mover 86. It is to be noted that the inner housing 24 does not rotate freely with respect to the outer housing 26 responsive to the prime mover 86.

To control operation of the prime mover 86, and thereby to control motion of the inner housing 24, a controller 102 is provided. Specifically, the controller 102 is electrically connected with the prime mover 86 by conductor 104. A sensor 106 is operatively associated with the inner housing 24 and electrically connected with the controller 102 by conductor 108 to provide the controller 102 with feedback indicative of movement of the inner housing 24. The controller 102 is electrically connected with the controller 16 by conductor 101 and with source 20 by conductor 103. Thus, the controller 102 and the controller 16 are able to positively regulate operation of the prime mover 86 to cause intended movement of the inner housing 24.

In an exemplary embodiment, the sensor 106 is a Hall effect sensor, such as model no. SS441A available from Allegro Semiconductor of Worcester, Mass. Other constructions for the sensor 106 are also possible. To provide a magnetic field for interaction with the sensor 106 in this embodiment, a magnet 110 (FIG. 2) is provided with the drive member 90. The magnet 110 may be model no. 18DRE2404 available from Magnet Sales & MFG. Co. of Culver City, Calif. In one embodiment, the magnet 110 is retained within a recess 112 in the drive member 90 by suitable means, such as an adhesive like an epoxy cement. In a specific embodiment, the recess 112 has a diameter of about 0.166 inches and is about 0.06 inches deep. The magnet 110 is oriented within the recess 112 such that a south pole of the magnet 110 faces the sensor 106. Thus, as the drive member 90 moves responsive to the operation of the prime mover 86, the magnet 110 generates a periodic electrical signal in the sensor 106. The electrical signal is substantially periodic with a frequency which is substantially equal to a rotational frequency of the drive shaft of the prime mover 86.

Figure 4:
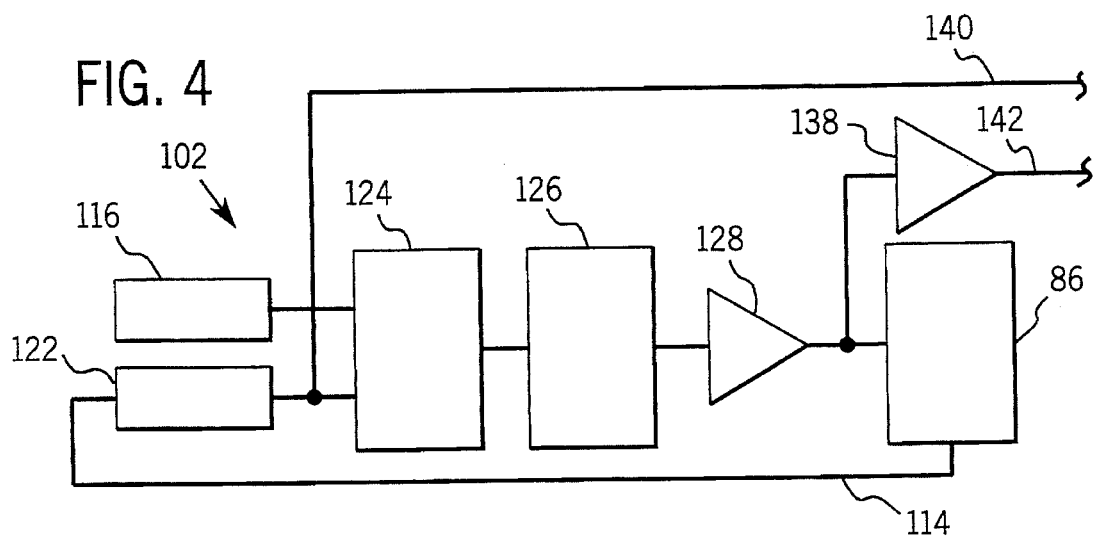
FIG. 4 is a block schematic diagram of a portion of the apparatus of FIG. 1.
Figure 6A:
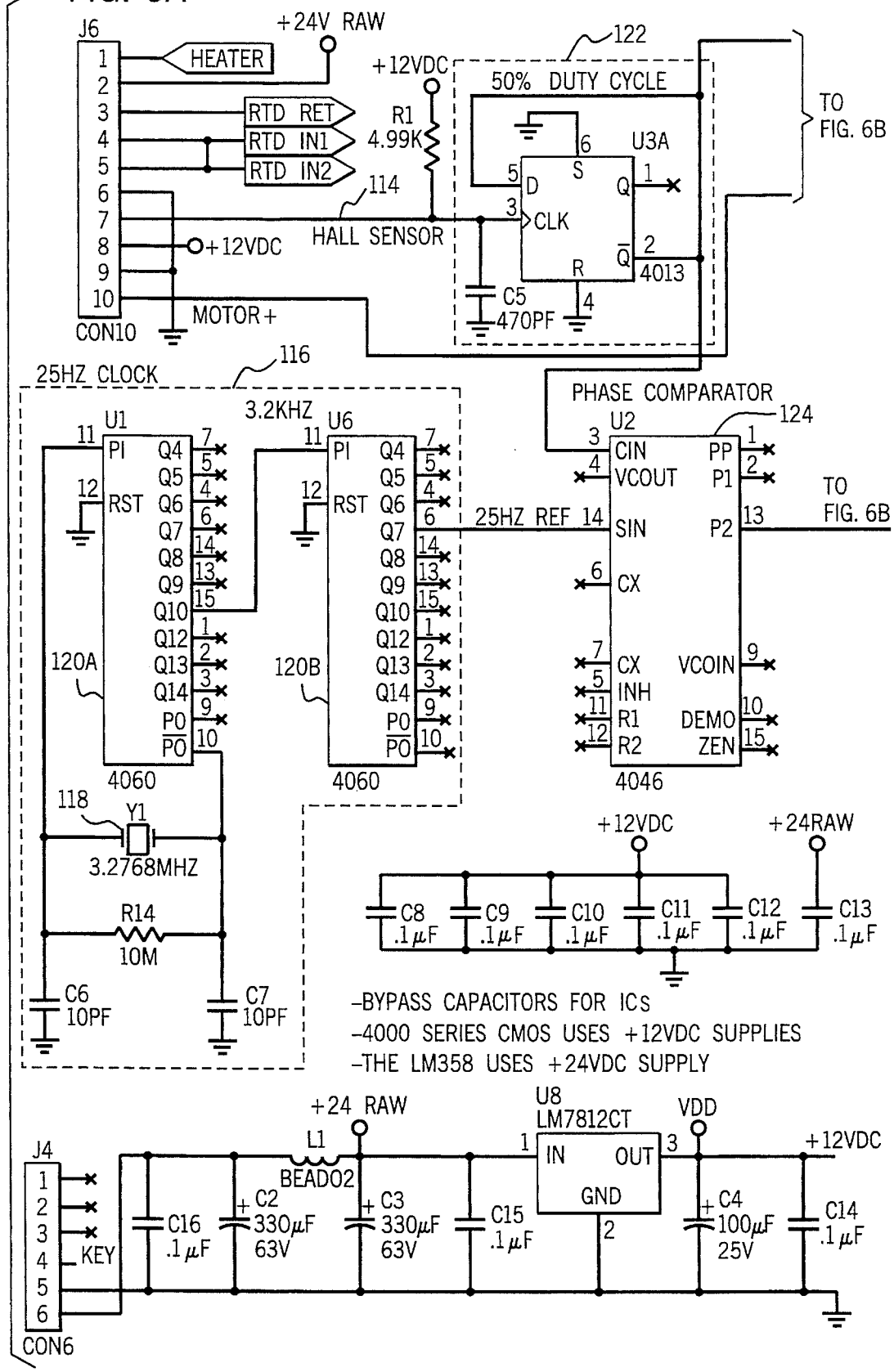
FIG. 6A and 6B are detailed schematic diagrams of the portion of the apparatus illustrated in FIG. 4.
Figure 6B:
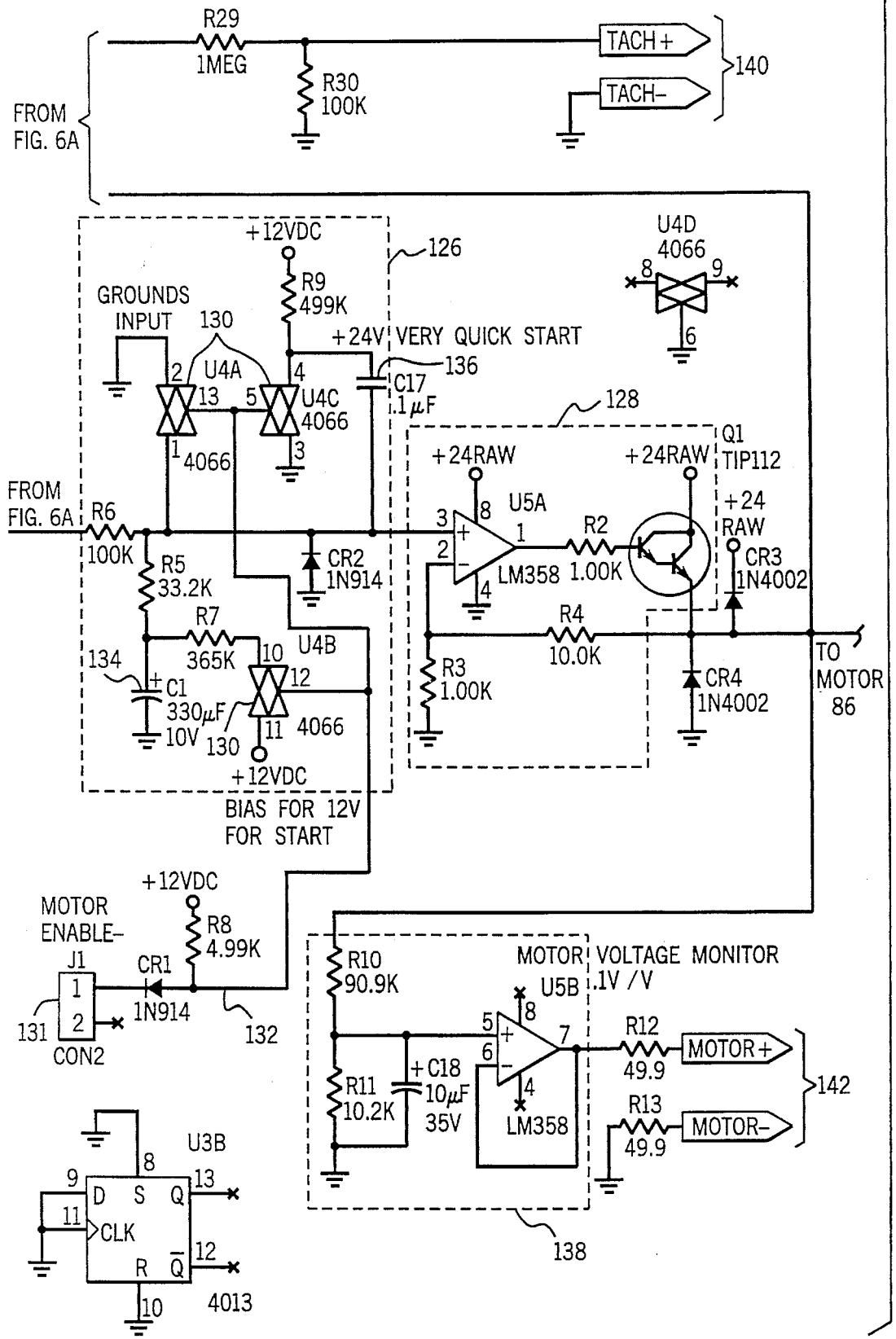

An exemplary embodiment of the controller 102 is illustrated in FIGS. 4 and 6. This embodiment generally operates by comparing a signal on conductor 114 indicating speed of the prime mover 86 to a reference signal and using a result of the comparison to drive the prime mover 86. The reference signal, produced in reference circuit 116, is, in one embodiment a square wave of about 25 Hertz. The reference circuit 116 comprises a crystal 118 (FIG. 6) which produces an electrical signal of about 3.2768 MHz, and two digital counters 120A and 120B electrically connected in series. The counters 120A and 120B may be, in one embodiment, 4060 14-stage counters, with the crystal 118 electrically connected between oscillator and clock pins of the counter 120A. In the illustrated embodiment, the Q10 output (which changes state about every $2^{10}$ or 1024 input cycles, yielding an approximately 3.2 kHz output) of the counter 120A is electrically connected with an input of the counter 120B. The Q7 output of the counter 120B changes state about every $2^7$ or 128 cycles of its input, yielding an approximately 25 Hz output.

The electrical signal on conductor 114, indicative of the prime mover 86 speed, is generated by the sensor 106. The signal on conductor 114 forms a clock input to a D flip-flop 122 configured to change states about every two clock cycles. The output of the flip-flop 122 is a square wave electrical signal with a frequency equal to about half of the rotational frequency of the drive shaft of the prime mover 86.

The reference signal from the reference circuit 116 and the output of the D flip-flop 122 are compared by a phase comparator 124. The phase comparator 124 may be a 4046 phase lock loop. The phase comparator 124 produces a relatively high signal output when the S input (the approximately 25 Hz reference signal) is of a higher frequency than the C input (the halved prime mover 86 rotational frequency). An output signal of the phase comparator 124 is low when the S input is of a lower frequency than the C input. When the frequencies applied to the S input and the C input are substantially equal, the output of the phase comparator 124 is a pulse train.

The output from the phase comparator 124 passes through a compensation network 126, with a dominant pole at about 0.005 Hz, and an amplifier 128, with a gain of about 11, to drive the prime mover 86.

The compensation network 126 also includes electronic switches 130 controlled by a negative enable prime mover signal from enabler 131 on conductor 132 that can ground the input of the amplifier 128 to deenergize the prime mover 86. When the negative prime mover enable signal from enabler 131 is high or disconnected, the switches 130 ground the amplifier 128 input. When the negative motor enable signal goes low, the switches 130 disconnect the input ground and enable prime mover 86 operation. A capacitor 134 which is biased with about +1.1 volts when the negative prime mover enable signal on conductor 132 is high, applies an initial voltage to the amplifier 128 when the negative prime mover enable signal on conductor 132 becomes low. A second capacitor 136 applies a short duration transient positive voltage to the amplifier 128 in order to initiate operation of the prime mover 86.

The controller 102 also provides output signals, one set from the D flip-flop 122 on conduits 140 and one set from the amplifier 128 via buffer 138 on conduits 142. The electrical signals on conduits 140 and 142 may be applied to the controller 16 via conductor 101. These output signals may be indicative of approximately half of the speed of the prime mover 86 and of about one-tenth of the prime mover 86 driver voltage. These output signals may be used for apparatus 10 monitoring and diagnostics.

With the construction of the apparatus being disclosed in detail, an example of operation of the apparatus 10 will now be given. It is to be noted that the following discussion is for illustrative purposes. For the sake of clarity, operation of the apparatus 10 is discussed with respect to an automated analytical instrument that can perform at least one of a white blood cell differential and immunophenotyping of lymphocytes in a whole blood sample.

It is assumed, for the sake of clarity, that the apparatus 10 is at rest (i.e. nothing is energized). An operator accesses the controller 16 to begin operation of the apparatus 10. A suitable first fluid, such as whole blood, a biological sample and the like, is made available to the fluid introducer 14. A suitable second fluid, such as a blood diluent, a lyse and the like, is made available at the source 50.

The controller 16 issues an electrical signal to the heater controller 60 via conductor 62 such that the heater controller 60 electrically connects the source 20 of electrical energy to the heating element 56. The electrical energy from the source 20 passes along conductors 68 and 58 to the heating element 56. The electrical energy is converted into thermal energy by the heating element 56. The thermal energy in the heating element 56 is transferred to the inner housing 24. In one embodiment, the heating element 56 is supplied with electrical energy until the sensor 64 detects that the thermal energy associated with the inner housing 24 is about 43 degrees Celsius (±1.5 degrees Celsius). By using a thermal energy level of less than about 45 degrees Celsius, in the case where the first fluid is whole blood, some blood cell surface antigens do not substantially denature and some blood proteins do not substantially coagulate. If sufficient blood cell surface antigens were to denature or if sufficient blood proteins were to coagulate, then those substances could coat portions of the apparatus 10 and the associated instrument. The coatings could dislodge variably and compromise operation of the apparatus 10 and the associated instrument.

The heater controller 60 maintains the desired thermal energy level associated with the inner housing 24 by regulating electrical energy flow from the source 20 of electrical energy to the heating element 56. Accordingly, the heater controller 60, and thus the heating element 56, may operate substantially continuously during operation of the apparatus 10 or the instrument with which the apparatus 10 is associated.

Once the inner housing 24 has the desired thermal energy level associated with it, the controller 16 sends an electrical signal to the controller 102 along conductor 101. Responsive to this electrical signal, the controller 102 electrically connects the prime mover 86 with the source 20 of electrical energy thereby energizing the prime mover 86. The prime mover 86 moves or vibrates the inner housing 24.

A predetermined volume of the second fluid, such as about 875 μl of lyse, is moved from the source 50 into the conduit 48 by a suitable mechanism, such as a syringe pump and the like. The second fluid flows through the fluid inlet 42 in the inner housing 24 toward the interior 28 of the inner housing 24. It is to be noted that, if desired, the prime mover 86 may be energized either before or after the predetermined volume of the second fluid is disposed within the interior 28 of the inner housing 24. The predetermined volume of second fluid moves conjointly with the inner housing 24 responsive to action of the prime mover 86 for a first predetermined time period, which may be on the order of about 5 seconds. After the first predetermined time period, the second fluid has substantially the same thermal energy as the inner housing 24.

The controller 16 sends an electrical signal to the fluid introducer 14 along conductor 18. The fluid introducer 14 acts to introduce a predetermined volume of first fluid, such as about 25 μl of whole blood, into the interior 28 of the inner housing 24. In one embodiment, the fluid introducer 14 may be a pipettor having a discharge nozzle which may be moved toward the opening 40 in the joining member 27. Once the discharge nozzle is in appropriate position with respect to the opening, the predetermined volume of first fluid is moved into the interior 28 of the inner housing 24.

Once the predetermined amount of first fluid is introduced into the interior 28 of the inner housing 24, the first fluid and the second fluid are moved within the inner housing 24 responsive to action of the prime mover 86 for a second predetermined time period which may be about 11 seconds. The prime mover 86 operates preferably at a frequency which is not equal to a resonant frequency associated with the apparatus 10.

In an exemplary embodiment, where the first fluid is whole blood and the second fluid is lyse, as described above, the first fluid and the second fluid substantially completely mix due to fluid movement within the inner housing 24 responsive to the prime mover 86. The ratio of first fluid to second fluid is about 1 to about 35. The red cells in the whole blood are relatively rapidly lysed and the white cells are relatively rapidly fixed, i.e. substantially preserving white cell morphology. Because the second fluid and the inner housing 24 are at substantially the same thermal energy level, the first fluid also reaches substantially the same thermal energy level after the second predetermined time period.

After the first and seconds fluids have been moved in the interior 28 of the inner housing 24 for the desired time period, operation of the prime mover 86 ceases. The mixture of the first fluid and the second fluid are moved through the fluid outlet 44 and conduit 52 toward the tank 54. The mixture is moved by an appropriate mechanism, such as a syringe pump, operatively associated with the fluid outlet 44. The mixture can be further processes or retained in the tank 54 until needed, The apparatus 10 is ready for further operation.

What is claimed is:

1. A method for preparing a solution made from a first predetermined volume of a first fluid and a second predetermined volume of a second fluid, the method comprising the steps of:

(a) operating a heater attached to a first housing and movable with the first housing for receiving the first fluid and the second fluid to apply thermal energy to the first housing, the first housing being operatively connected with and disposed substantially within a second housing;

(b) introducing the second predetermined volume of the second fluid to the first housing;

(c) vibrating the first housing with a prime mover to move the second predetermined volume of the second fluid in the first housing for a first predetermined time period while second housing remains substantially stationary with respect to the prime mover;

(d) introducing the first predetermined volume of the first fluid to the first housing;

(e) vibrating the first housing with the prime mover to move the first predetermined volume of first fluid and the second predetermined volume of second fluid in the first housing for a second predetermined time period to make the solution while the second housing remains substantially stationary with respect to the prime mover; and (f) removing the solution made from the first predetermined volume of first fluid and the second predetermined volume of second fluid from the first housing.

2. A method as defined in claim 1 wherein the first predetermined volume is about 25 μl.

3. A method as defined in claim 1 wherein the first fluid is a whole blood sample.

4. A method as defined in claim 1 wherein the second predetermined volume is about 875 μl.

5. A method as defined in claim 1 wherein the second fluid is a blood diluent.

6. A method as defined in claim 1 wherein the first predetermined time period is about 5 seconds.

7. A method as defined in claim 1 wherein the second predetermined time period is about 11 seconds.

8. A method as defined in claim 1 wherein the first fluid is whole blood including red blood cells and white blood cells and the second fluid is a blood diluent and further comprising the steps of:

(g) lysing the red blood cells; and (h) fixing the white blood cells.

9. A method as defined in claim 1 further comprising the step of:

(g) storing the first predetermined volume of first fluid and the second predetermined volume of second fluid removed from the first housing.

10. A method as defined in claim 1 wherein the thermal energy applied to the first housing is about 43 degrees Celsius.

11. A method as defined in claim 1 further comprising the step of:

(g) applying thermal energy from the first housing to at least one of the first fluid and the second fluid.

12. A method of preparing a fluid, the method comprising the steps of:

(a) placing the fluid within a first housing, the first housing being operatively connected with and being disposed substantially within a second housing;

(b) applying thermal energy to the first housing and the fluid within the first housing with a heater attached to and movable with the first housing; and (c) vibrating the first housing with a prime mover to move the fluid contained in the first housing while the second housing remains substantially stationary with respect to the prime mover.

13. A method as defined in claim 12 further comprising the step of:

(d) removing fluid from the first housing.

14. A method as defined in claim 12 further comprising the step of:

(d) applying thermal energy to the fluid before the fluid is placed within the first housing.

15. An apparatus for preparing a fluid comprising:

(a) a first housing for containing fluid;

(b) a second housing operatively connected with the first housing such that the first housing is disposed substantially within the second housing;

(c) a prime mover fixedly attached to the second housing and operatively connected with the first housing such that the first housing moves responsive to the prime mover and such that the second housing remains substantially stationary with respect to the prime mover;

(d) a heater thermally connected and movable with the first housing for applying thermal energy to the first housing;

(e) a fluid inlet fluidly connected with the first housing for supplying fluid to the first housing; and (f) a fluid outlet fluidly connected with the first housing for removing fluid from the first housing.

16. An apparatus as defined in claim 15 further comprising:

(g) a joining member operatively connecting an open end of the first housing and an open end of the second housing.

17. An apparatus as defined in claim 16 wherein the joining member is made of an elastomer.

18. An apparatus as defined in claim 15 further comprising (g) a sensor thermally connected and movable with the first housing for detecting thermal energy associated with the first housing.

19. An apparatus as defined in claim 15 further comprising (g) a source of a blood diluent fluidly connected with the fluid inlet.

20. An apparatus as defined in claim 15 further comprising (f) a sensor operatively associated with the prime mover for detecting operation of the prime mover.

21. An apparatus as defined in claim 15 further comprising (g) a linkage assembly drivingly connecting the prime mover and the first housing; the linkage assembly being constructed such that the first housing moves substantially eccentrically responsive to the prime mover.

22. An apparatus as defined in claim 15 further comprising (g) a fluid introducer operatively associated with the first housing for introducing a fluid into the first housing.

23. An apparatus as defined in claim 22 further comprising (h) a source of whole blood fluidly connected with the fluid introducer such that whole blood is introduced into the first housing by the fluid introducer.

24. An apparatus as defined in claim 15, the apparatus further comprising:

(g) a source of whole blood operatively connected with the first housing for supplying the first housing with whole blood; and (h) a source of a blood diluent operatively connected with the first housing for supplying the first housing with blood diluent.

* * * * *

UNITED STATES PATENT AND TRADEMARK OFFICE
CERTIFICATE OF CORRECTION

PATENT NO. : 5,589,394
DATED : December 31, 1996
INVENTOR(S) : Kim, et. Al.

It is certified that error appears in the above-indentified patent and that said Letters Patent is hereby corrected as shown below:

In the abstract, line 17, change "fixedly-attatched" to --fixedly attatched--.

Column 10, line 21, change "while" to --while the--.

Signed and Sealed this

Twenty-seventh Day of May, 1997

Attest:

BRUCE LEHMAN

Attesting Officer

Commissioner of Patents and Trademarks